United States Patent [19]

Vidrine, Jr. et al.

[11] Patent Number: 4,827,121
[45] Date of Patent: May 2, 1989

[54] SYSTEM FOR DETECTING CHEMICAL CHANGES IN MATERIALS BY EMBEDDING IN MATERIALS AN UNCLAD FIBER OPTIC SENSOR SECTION

[75] Inventors: Warren D. Vidrine, Jr., San Jose; Mark S. Roth, Palo Alto, both of Calif.

[73] Assignee: Measurex Corporation, Cupertino, Calif.

[21] Appl. No.: 159,154

[22] Filed: Feb. 24, 1988

[51] Int. Cl.⁴ .................... H01T 5/16; G01N 21/41
[52] U.S. Cl. .................................. 250/227; 356/133
[58] Field of Search .............. 250/227, 573, 576; 356/133, 409, 414

[56] References Cited

U.S. PATENT DOCUMENTS 4,608,344  8/1986  Carter et al. .................. 356/414
4,639,594  1/1987  Schoch et al. ................. 250/227

Primary Examiner—David C. Nelms
Assistant Examiner—William L. Oen

[57] ABSTRACT

A system for detecting chemical characteristics within a material includes an optical fiber having a relatively short unclad sensor section for embedding in a material, a source of infrared radiation to direct infrared radiation into the fiber, and an optical decoder connected to the fiber to detect the spectrum of infrared radiation absorbed by the material in which the sensor section is embedded.

37 Claims, 1 Drawing Sheet

U.S. Patent   May 2, 1989   4,827,121
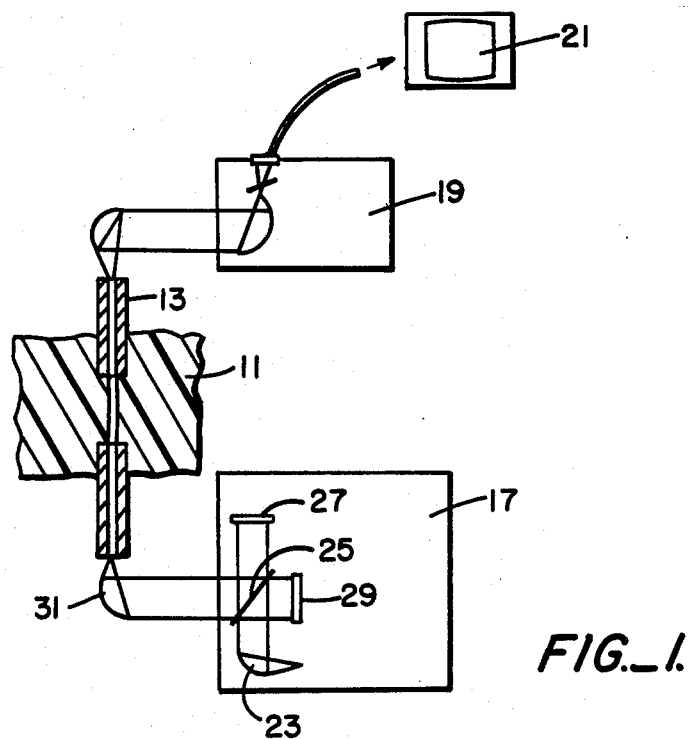
FIG._1.
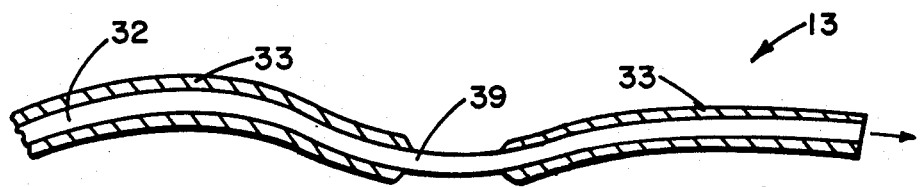
FIG._2.
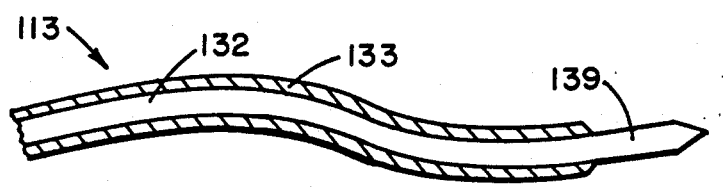
FIG._3.

SYSTEM FOR DETECTING CHEMICAL CHANGES IN MATERIALS BY EMBEDDING IN MATERIALS AN UNCLAD FIBER OPTIC SENSOR SECTION

BACKGROUND OF THE INVENTION

1. Field of the Invention

The present invention generally relates to sensors for detecting chemical characteristics of materials and, more particularly, to sensors for use with spectrometric systems.

2. State of the Art

It is often desirable to monitor chemical changes in materials during manufacture. This is especially true in the case of modern composite materials which, if properly manufactured, can have the same strength and stiffness as comparable monolithic materials but with significantly less weight.

In the manufacture of items made from fiberreinforced composite materials, combinations of fiber and polymer resins are employed to form plies, or laminations, which are stacked in predetermined orientations. After stacking, the composite material is cured, usually at high temperatures in an autoclave, to cross-link the polymers in a desired manner. The curing process is usually referred to as "thermosetting". The properties of the composite materials can be selectively altered by changing the fiber and polymer resin matrix components, by changing the fiber orientations, or by changing the manner or extent of cross-linking of the polymer resins. In particular, cross-linking is affected by manufacturing process conditions, primarily temperature and pressure.

Although fiber-reinforced composites can be produced having extraordinary structural characteristics, it is often difficult to develop volume production techniques which reliably produce composite materials having uniform structural properties run-after-run. Frequently, the difficulties in obtaining reproducibility can be traced to inadequate process-control information. Inadequacies in process control information during production can lead to high inspection costs and can result in a substantial portion of a production run being discarded as sub-standard.

In response to the need for process control information during production of fiber-reinforced composite materials, a technique called dielectric cure monitoring has been developed. According to this technique, sensing wires are embedded in a composite material and dieletric permittivity is measured during curing. Dielectric cure monitoring has the advantage that it is a "real-time" process, which is to say that measurements are made simultaneously with the monitored events and, therefore, nearly simultaneous process interventions (e.g., changes in temperature and pressure) can be effected. Unfortunately, dielectric cure monitoring has the drawback that extraneous factors, such as mechanical voids and moisture absorption, often interfere with measurements and cause spurious results. Also, although dielectric cure monitoring is generally thought of as a non-destructive testing technique, embedded dielectric sensing wires can cause micro-cracking of a composite material.

Another technique which has been used to detect conditions of composite materials during thermosetting is Fourier transform infrared (FT-IR) spectroscopic monitoring. This technique is described in a paper entitled "FTIR Characteristics of Advanced Materials" presented by P. Young and A. Chang at SAMPE, Las Vegas, Nev., Apr. 8-10, 1986. In the technique described by Young and Chang, infrared radiation is directed against the surface of a composite material and reflected radiation is collected and measured. By spectrometric analysis of changes in reflected radiation during the cure cycle, Young and Chang were able to determine which wavelengths were absorbed by the monitored material. The spectrometric information was then correlated with cure conditions and, hence, with cross-linking of polymer resins in the composite materials.

A shortcoming of FT-IR cure monitoring as practiced by Young and Chang, supra, is that chemical characteristics were only detected near the surface of composite materials. In practice, surface conditions are not necessarily representative of conditions at substantial depths within items formed of composite materials and, therefore, FT-IR spectroscopic analysis as practiced by Young and Chang does not always fully indicate whether resins are being properly cross-linked (i.e., cured) within the various plies of composite materials.

In view of the preceding, it can be understood that there exists a need for techniques whereby chemical changes, such as during curing, can be directly monitored at substantial depths within an item fabricated from a material such as a fiber-reinforced composite.

BRIEF DESCRIPTION OF THE DRAWINGS

FIG. 1 is a schematic diagram of a system according to the present invention;

FIG. 2 is a cross-sectional view, enlarged for purposes of clarity, of a sensor for use in the system of FIG. 1; and FIG. 3 is a cross-sectional view, enlarged for purposes of clarity, of an alternative embodiment of a sensor for use in the system of FIG. 1.

DETAILED DESCRIPTION OF PREFERRED EMBODIMENT

FIG. 1 shows a spectrum analysis system for measuring chemical conditions within a material. The system is particularly useful for detecting the degree of cross-linking of resins within a fiber-reinforced composite material during curing, but its utility is not limited to such applications. The system could be employed, for example, to detect chemical states in fluids, including gasses and liquids, as well as in solids which are not adversely affected by the presence of embedded optical fibers.

Generally speaking, the components of the spectrum analysis system illustrated in FIG. 1 include one or more optical fibers 13 which are embedded at preselected locations within a section of material 11, a light encoder 17 which is connected to transmit optical radiation into the fibers 13, a detector 19 which is connected to receive optical radiation emerging from the fibers, and a light decoder 21 which is connected to analyze the detected optical radiation. As will be described in detail below, each optical fiber 13 includes a sensor section.

It should be understood that optical fibers 13 and material 11 are located exterior of decoder 21. In other words, the system of FIG. 1 neither requires that relatively small samples of material 11 be obtained for analysis within the decoder nor that the decoder be placed within a hostile environment, such as an autoclave, to produce spectrum analysis.

Generally speaking, decoder 21 is a device which discriminates among, or decodes, at least a part of the spectrum of input signals. (Although signals physically exist in the time domain, they can be analyzed as consisting of sinusoidal components having various frequencies and amplitudes, i.e., spectrums.) In the preferred embodiment, decoder 21 is a so-called Fourier transform infrared (FT-IR) spectrometer. Generally speaking, a Fourier transformation (FT) spectrometer is a spectrometer which employs mathematical techniques based upon Fourier analysis to analyze time-domain signals to arrive at their spectral description. A Fourier transform infrared (FT-IR) spectrometer is a spectrometer which decodes the frequency components of infrared signals by Fourier analysis. Such spectrometers are commercially available from various sources and are usually based upon microprocessors.

Alternatively, decoder 21 can be embodied as another conventional device which discriminates between different wavelengths of light. For example, decoder 21 can be a monochrometer. As another example, decoder 21 can comprise an array of photometers, each of which detects different wavelengths of light. It should be noted, however, that such devices are generally less accurate than FT-IR spectrometers.

In practice, it is preferred that spectrometric information is obtained in the system of FIG. 1 from mid-infrared light. In this context, mid-infrared light means light having wavelengths ranging from about two to about twenty microns. The wavelength band of interest for FT-IR spectrometric analysis is usually from about five to about fifteen microns, which is sometimes called the "fingerprint" region.

The purpose of encoder 17 is to modulate, or encode, light which is directed into an optical fiber 13. In the illustrated embodiment, encoder 11 comprises an interferometer having a light source 23, a half-silvered mirror 25 positioned to receive light from source 23, and a pair of mirrors 27 and 29 positioned to receive transmitted and reflected light, respectively, from half-silvered mirror 25. At least one of the mirrors 27 and 29 is selectively moveable relative to the other to provide wavelength displacements and, hence, encoding. Together, the three mirrors 25, 27 and 29 function to direct light onto a fourth mirror 31 which, in turn, directs the light into the adjacent end of optical fiber 13.

At this juncture, it should be appreciated that a light encoder other than an interferometer can be used in the system of FIG. 1. For example, a spectral grating device can be used. The critical criteria for such encoding devices is that they modulate, or encode, light for analysis by spectrometer 21.

Also, it should be understood that a light encoder need not be mounted at the same end of an optical fiber as the light source. In fact, the encoder could be mounted at the same end of an optical fiber as the light decoder as long as the encoder is interposed between the end of the fiber and the decoder.

The detector 19 in the system of FIG. 1 can be any one of several conventional transducer devices. For example, detector 11 can be a conventional pyro-electric detector or a conventional photo-electric detector which converts light to electrical signals. Generally speaking, the purpose of detector 19 is to non-selectively detect infrared radiation over a band of wavelengths at least as broad as the band of interest to decoder 21.

Referring now to FIG. 2, there are shown details of an optical fiber 13. Generally speaking, the illustrated fiber includes a glass core 32 and a thin cladding 33 which forms a sheath around the core. The cladding 33 has the purpose of preventing light from entering or leaving the sides of the core. Although various cladding materials can be used, the most suitable ones have refractive indices which provide high total internal reflection of infrared light at the cladding-core interface. This requirement can also be stated conversely by saying that the preferred cladding materials do not provide strong internal absorption of infrared light.

In the embodiment illustrated in FIG. 2, cladding 33 extends the entire length of core 32 except for an unclad section 39 where core 32 is exposed directly to material 11. The unclad section 39 can be called the "sensor section" to denote its function in the system of FIG. 1. Typically, the diameter of sensor section 39 ranges from about fifty to about three hundred microns. In practice, sensor section 39 can be formed either by removing cladding 33 from core 32 or by fusing an unclad core section to optical fiber. As to the latter alternative, it should be understood that the remainder of the optical fiber need not be made of the same material as sensor section 32 although, in the preferred embodiment, the material of the sensor section is the same as the remainder of the optical fiber.

As to its optical properties, sensor section 32 should be formed of a material which transmits light without substantial attenuation in the wavelengths that provide the most meaningful signal information to decoder 21. As to its physical properties, sensing section should be formed of a material that can withstand embedding in a fiber-reinforced composite material during curing; quantitatively, this can be expressed by saying the glass transition temperature, Tg, of the core material should exceed about three-hundred-fifty ° C. Also, sensor section 32 should be formed of a material which has high indices of refraction relative to the material in which the fiber is embedded over the wavelengths of interest. For example, it is desirable that the refractive indices exceed about 2.0 for a fiber-reinforced composite material. In this regard, it can be noted that refractive indices vary with wavelength for a given material.

The presently preferred core material for sensing section 13 is chalcogenide glass, and, for example, arsenic germanium-selenide glass. Not only can chalcogenide glass fibers be obtained commercially that survive normal curing temperatures in an autoclave but also chalcogenide glass has high refractive indices (normally greater than 2.0) relative to most fiber-reinforced composite materials at the mid-infrared wavelengths. Suitable chalcogenide glass fibers can be commercially obtained from various sources.

Another material suitable for sensing section 32 is metal floride glass. Floride glass materials are commercially available that provide relatively small transmission losses (e.g., less than 100 dB per kilometer) and have a glass transition temperature of about 350° C. Because metal floride glass fibers provide relatively little attenuation of light, such fibers can be used for FT-IR analysis of near-infrared light, i.e., light having wavelengths ranging from about one to five microns.

Operation of the system of FIG. 1, will now be described in the case where the optical fiber of FIG. 2 is employed. Initially, it should be assumed that at least one optical fiber 13 has been embedded in a material which is to undergo processing, such as by autoclaving, and that the embedding material 11 directly contacts the sensor section 39 of the fiber. It should also be initially assumed that encoder 17 is operated to modulate light passing into, or out of, an end of the fiber. Under such conditions, the light travels through the fiber until it reaches the unclad sensor section 39. Along the unclad sensor section, light which is incident upon the sidewall of core 32 of the fiber is partly reflected and partly refracted by the surrounding material. The extent of reflection and refraction depends upon the characteristics of sensor section 39 as well as upon the nature and state of the surrounding material 11. Moreover, the extent of reflection and refraction varies with chemical changes of the surrounding material, and the extent of changes in reflection and refraction at some wavelengths of light may be substantially different than at other wavelengths. Stated in more technical terms, it can be said that behavior of light at the sensor section is described by a phenomenon known as attenuated total reflection (ATR). In the ATR phenomenon, reflected light is assumed to penetrate the reflecting surface sufficiently that the electric vector of the light interacts with chemical bonds in the material of the reflecting surface. In the literature, the ATR phenomenon is sometimes referred to as "frustrated total internal reflection" or the acronym FTIR.

Further in operation of the system of FIG. 1, light which is reflected at the interfaces between the unclad sensor section and the surrounding material is carried to detector 19. Then, detector 19 converts light at the various wavelengths to corresponding electrical signals. The electrical signals from detector 19 are transmitted to decoder 21 which analyzes the spectrum of the signals. (When more than one optical fiber is employed, signals from each of the fibers can be separately analyzed through the use of conventional multiplexing techniques.) Analysis of the spectrums can be used, for example, as the basis for changing process conditions such as the temperature and pressure within an autoclave.

Referring now to FIG. 3, there is shown an optical fiber 113 having a sensing section 139 which is geometrically different, but functionally equivalent, to the sensing section 39 of the fiber of FIG. 2. In FIG. 3, optical fiber 113 is surrounded by cladding 133 except for unclad sensing section 139 at the tip of the fiber. Preferably, the unclad tip has a conical or pyramidal shape. Alternatively, however, the unclad tip can have a flat, polished end.

The optical fiber 113 of FIG. 3 can be employed in a spectrometric system similar to the system of FIG. 1 except that a light source and decoder 21 will be located at the same end of the fiber. Ordinarily, this will be accomplished by providing a beam splitter to separate source light from received light. Beam splitters which perform such a function are well known.

Although a preferred embodiment of the present invention has been illustrated and described, various modifications, alternatives, and equivalents thereof will become apparent to those skilled in the art. Most importantly, it should be recognized that the above-described spectrometric system can be used for in-situ, real-time detection of the chemical state of materials other than fiber-reinforced composites. Also, the utility of the above-described system extends to any environment where chemical changes occur, including relatively slow changes such as fatigue in structural components.

What is claimed is:

1. A system for detecting chemical characteristics within a material comprising:
    an optical fiber embedded in a material, the fiber having an unclad sensor section;
    source means connected to direct optical radiation into the fiber;
    encoding means to modulate the optical radiation; and
    spectrum analyzer means connected to the fiber to detect at least a part of the spectrum of the modulated optical radiation and, thereby, to detect chemical characteristics of the material in which the sensor section is embedded.

2. A system according to claim 1 wherein the unclad sensor section comprises a section between the ends of the fiber, and the source of means is connected to one end of the fiber and the spectrum analyzer means is connected to the other end of the fiber.

3. A system according to claim 1 wherein the unclad sensor section is at the end of the fiber, and the source means of infrared radiation and the spectrum analyzer are connected to the same end of the fiber.

4. A system according to claim 1 wherein the optical fiber extends outside the spectrum analyzer means.

5. A system according to claim 3 wherein the tip of the unclad sensor section of the fiber is generally pointed.

6. A system according to claim 1 wherein the spectrum analyzer means comprises a Fourier transform analyzer.

7. A system according to claim 1 wherein the encoding means comprises an interferometer.

8. A system according to claim 1 wherein unclad sensor section is formed from chalcogenide glass.

9. A system according to claim 8 wherein the chalcogenide glass is arsenic germanium-selenide glass.

10. A system according to claim 1 wherein the sensor section is formed from metal floride glass.

11. A system for providing in-situ detection of the chemical state within a fiber-reinforced composite material, comprising:
    an optical fiber embedded in the fiber-reinforced composite material, the fiber having an unclad sensor section and the remainder of the fiber being clad;
    a light source connected to direct infrared radiation into the fiber;
    a detector connected to detect infrared radiation emerging from an end of the fiber; and
    a spectrum analyzer connected to the detector for measuring at least a part of the spectrum of infrared radiation absorbed by the composite material adjacent the sensor section.

12. A system according to claim 11 wherein the unclad sensor section comprises a section intermediate the ends of the fiber, and the light source is connected to one end of the fiber and the spectrum analyzer is connected to the other end of the fiber.

13. A system according to claim 11 wherein the unclad sensor section is at the end of the fiber.

14. A system according to claim 13 wherein the light source and the spectrum analyzer are in optical communication with the same end of the fiber via a beam splitter.

15. A system according to claim 11 wherein the spectrum analyzer comprises a Fourier transform analyzer.

16. A system according to claim 11 further including an interferometer disposed between the sensor section and the spectrum analyzer.

17. A process for detecting chemical characteristics within a material, comprising the steps of:
- forming an optical fiber having an unclad sensor section;
- embedding the sensor section of the optical fiber in a material to be analyzed;
- directing light into the fiber; and
- operating a spectrum analyzer connected to the fiber to analyze at least a part of the spectrum of infrared radiation absorbed by the material adjacent the sensor section.

18. A process according to claim 17 wherein the material is a thermosettable matrix resin.

19. A process according to claim 18 wherein the analyzer is operated while curing the resin.

20. A process according to claim 19 wherein the analyzer measures the degree of cross-linking of the resin.

21. A process according to claim 17 wherein a plurality of the optical fibers, each having a sensor section, are embedded in the materials at selected locations.

22. A process according to claim 17 wherein the material to be analyzed is located external of the analyzer.

23. A process according to claim 22 wherein the analyzer is a Fourier transform infrared analyzer.

24. A process according to claim 23 wherein the analyzed radiation is in the mid-infrared spectrum.

25. A process according to claim 24 wherein the wavelengths of analyzed radiation ranges from about five to about fifteen microns.

26. A process according to claim 25 wherein the spectrum analysis is accomplished by measuring attenuated total reflection.

27. A process according to claim 17 wherein the unclad sensor section is connected between the ends of the fiber, and light is directed into one end of the fiber and the spectrum analyzer is connected to the other end of the fiber.

28. A process according to claim 17 wherein the unclad sensor section is at the end of the fiber.

29. A process according to claim 17 wherein the core of the optical fiber is formed from chalcogenide glass.

30. A process according to claim 17 wherein the core of the optical fiber is formed from metal floride glass.

31. A process for providing in-situ detection of chemical conditions within a fiber-reinforced composite material during curing, comprising:
- embedding an optical fiber in the fiber-reinforced composite material with at least one end of the fiber extending from the material, the fiber having an unclad sensor section and the remainder of the fiber being clad;
- connecting a source of infrared radiation to the fiber; and
- connecting a Fourier transform spectrum analyzer to the fiber for detecting the spectrum of infrared radiation absorbed by the composite material adjacent the unclad sensor section.

32. A process according to claim 31 wherein the unclad sensor section is formed by removing cladding from the fiber.

33. A process according to claim 32 wherein the unclad sensor section is formed by fusing an unclad optical fiber to a clad optical fiber.

34. A process according to claim 32 wherein the unclad sensor section is at the end of the fiber.

35. A process according to claim 32 wherein the unclad sensor section is between the ends of the fiber.

36. A sensor for use with a spectrum analyzer for detecting the chemical state of materials external to the spectrometer comprising:
- an optical fiber having an unclad sensor section for insertion into a material whose chemical state is to be measured and an end adapted for connection to a spectrum analyzer.

37. A sensor according to claim 36 wherein the material comprising the sensor section is compatible with Fourier transform infrared spectrum analyzer.

* * * * *

Notice of Adverse Decisions in Interference

In Interference No. 102,521, involving Patent No. 4,827,121, Warren D. Vidrine Jr., Mark S. Roth, SYSTEM FOR DETECTING CHEMICAL CHANGES IN MATERIALS BY EMBEDDING IN MATERIALS AN UNCLAD FIBER OPTIC SENSOR SECTION, final judgement adverse to the patentees was rendered Aug. 5, 1991, as to claims 1-37.

*(Official Gazette Oct. 22, 1991)*